(12) United States Patent
Kochamba et al.

(10) Patent No.: US 7,237,555 B2
(45) Date of Patent: Jul. 3, 2007

(54) TISSUE STABILIZATION AND ABLATION DEVICES AND METHODS

(75) Inventors: Gary S. Kochamba, Studio City, CA (US); Suzanne E. Kochamba, Studio City, CA (US); Arthur A. Bertolero, Danville, CA (US)

(73) Assignee: Estech, San Ramon, CA (US)

( * ) Notice: Subject to any disclaimer, the term of this patent is extended or adjusted under 35 U.S.C. 154(b) by 878 days.

(21) Appl. No.: 10/272,541

(22) Filed: Oct. 15, 2002

(65) Prior Publication Data

US 2003/0125604 A1 Jul. 3, 2003

Related U.S. Application Data

(63) Continuation-in-part of application No. 09/268,556, filed on Mar. 15, 1999, now Pat. No. 6,607,479, which is a continuation-in-part of application No. 09/042,853, filed on Mar. 17, 1998, now Pat. No. 6,251,065.

(51) Int. Cl.
*A61B 19/00* (2006.01)
*A61B 18/14* (2006.01)

(52) U.S. Cl. ........................................ 128/898; 606/41
(58) Field of Classification Search .................... 606/41
See application file for complete search history.

(56) References Cited

U.S. PATENT DOCUMENTS

| | | |
|---|---|---|
| 3,745,998 A | 7/1973 | Rose |
| 5,727,569 A | 3/1998 | Benetti et al. |
| 5,782,746 A | 7/1998 | Wright |
| 5,807,243 A | 9/1998 | Vierra et al. |
| 5,836,311 A | 11/1998 | Borst et al. |
| 5,927,284 A | 7/1999 | Borst et al. |

OTHER PUBLICATIONS

Octopus™ Tissue Stabilizer and Accessory Products, "Defining the Future of Minimally Invasive and Beating Heart Cardiac Surgery", Jan. 15, 1998.
Medtronic Advertisement, Aug. 1997, The Annals of Thoracic Surgery.

*Primary Examiner*—Lee S. Cohen
(74) *Attorney, Agent, or Firm*—Townsend and Townsend and Crew LLP

(57) ABSTRACT

Tissue stabilization and ablation devices and methods provide techniques for stabilizing and ablating body tissues during surgical ablation procedures. In many embodiments, for example, devices may be used in minimally invasive techniques for ablating epicardial tissue adjacent one or more pulmonary veins to treat atrial fibrillation. Tissue stabilization and ablation devices generally include a rigidifying bladder coupled with an ablation member. The devices may additionally include a tissue stabilizing bladder or means within the rigidifying bladder for enhancing tissue stabilization. The rigidifying bladder conforms to a tissue surface and then stiffens to help the device hold its shape and position and to stabilize the tissue. The ablation member is then used to ablate an area of tissue. Such cardiac stabilization and ablation devices and methods may be used to ablate one or more patterns on the epicardial surface of a heart to treat atrial fibrillation and/or other cardiac arrhythmias.

23 Claims, 11 Drawing Sheets

TISSUE STABILIZATION AND ABLATION DEVICES AND METHODS

CROSS-REFERENCES TO RELATED APPLICATIONS

The present application is a continuation-in-part of U.S. patent application Ser. No. 09/268,556, filed Mar. 15, 1999, now U.S. Pat. No. 6,607,479, which is a continuation-in-part of U.S. patent application Ser. No. 09/042,853, filed Mar. 17, 1998, now U.S. Pat. No. 6,251,065 B1, the entire contents of which are hereby incorporated by reference.

BACKGROUND OF THE INVENTION

The present invention relates generally to medical devices and methods. More specifically, the invention relates to devices and methods for stabilizing and ablating body tissues, such as cardiac tissue, to treat various conditions, such as atrial fibillation.

Atrial fibrillation (AF) is a heart beat rhythm disorder in which the upper chambers of the heart known as the atria quiver rapidly, instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3% of those aged 50-59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be under-prescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Currently available devices and methods, however, do not provide ideal means for cardiac stabilization and ablation of epicardial tissue in advantageous patterns for treating AF. Although many ablation devices and stabilization devices are currently available, combining stabilization and ablation features into one device to allow ablation of epicardial tissue in a desired pattern on a beating heart has proven challenging. Typically, therefore, current cardiac ablation procedures for AF treatment still require stopping the heart and using a cardiopulmonary bypass apparatus.

Therefore, a need exists for devices and methods to enhance minimally invasive techniques for ablating cardiac tissue to treat AF. Preferably, such devices and methods would provide ablation in one or more patterns on the epicardial surface of the heart, such as in a pattern adjacent to or surrounding one or more pulmonary veins. Also preferably, the devices and methods would provide stabilization of the heart as well as ablation, to allow for minimally invasive ablation procedures without cardiopulmonary bypass. At least some of these objectives will be met by the present invention.

BRIEF SUMMARY OF THE INVENTION

Devices and methods of the present invention provide for stabilization and ablation of a body tissue. In some embodiments, for example, devices and methods are used to stabilize and ablate epicardial tissue to treat atrial fibrillation (AF). Stabilization/ablation devices generally include a rigidifying bladder coupled with a tissue securing bladder having one or more ablation elements. In some embodiments, however, devices may include one bladder divided into rigidifying and tissue securing elements. Rigidifying and/or securing bladders may be coupled with one or more engaging members for engaging a stabilization/ablation device with one or more positioners used for positioning the device on a tissue. Generally, bladders and engaging members allow for positioning and securing of the device onto an area of tissue and for stabilizing the tissue during an ablative procedure.

Ablation of tissue, such as epicardial tissue in a pattern around or in proximity to one or more pulmonary veins, may eliminate or ameliorate AF. Ablation of epicardial or other tissues in various other patterns may have other beneficial effects. Generally, any suitable means for tissue ablation may be used in the present invention, such as but not limited to transmission of radio frequency energy, cryogenic energy, microwave energy, laser energy or ultrasound energy. To enhance the efficacy of ablation procedures using the devices and methods of the present invention, various embodiments include one or more sensors for detecting ablation of a tissue, cooling members for cooling a tissue and/or the ablation device, visualization means such as an and/or the like.

In one aspect of the present invention, a method of stabilizing and ablating body tissue includes contacting a tissue stabilizer having a non-rigid bladder with the tissue, securing the tissue stabilizer to the tissue, rigidifying the bladder, and applying ablation energy to at least a portion of the tissue through the rigidified bladder. In some embodiments, rigidifying the bladder comprises applying a vacuum to the bladder, wherein the vacuum collapses the bladder to cause the bladder to rigidify. Optionally, the vacuum may be applied to the tissue through at least one aperture in the bladder to enhance securing of the tissue stabilizer to the tissue. For example, the vacuum may be applied to the tissue through a separate tissue securing bladder coupled with the rigidified bladder. Alternatively, the vacuum may be applied to the tissue through a tissue securing compartment in the rigidified bladder.

In many embodiments, the rigidifying bladder will further include at least one port, a chamber within the bladder and in communication with the port, and rigidifying structure disposed within the chamber. The rigidifying structure is generally configured to be substantially flexible when no suction is applied at the port and substantially rigid when suction is applied at the port.

As discussed further below, the tissue that is stabilized and ablated may be any suitable body tissue, of a human, animal, cadaver, or the like. Frequently, the tissue will be heart tissue adjacent at least one pulmonary vein, as in the treatment of AF. For example, epicardial tissue near two pulmonary veins will often be stabilized and ablated with embodiments of the invention.

Contacting of the device with the tissue to be stabilized and ablated may be accomplished by any suitable means. In some embodiments, where a heart tissue is ablated, the heart may be accessed and contacted via a conventional surgical approach, such as via a median sternotomy. In other embodiments, the device may be positioned for contact with heart tissue via minimally invasive means, such as by folding a flexible device and inserting it through a trocar sheath. Similarly, devices and methods of the present invention may be used as part of any suitable cardiothoracic surgical procedure or cardiovascular intervention, such as beating heart surgery or surgery involving cardiopulmonary bypass.

Ablating tissue with the ablation member may include any suitable means of ablation. For example, various embodiments may include radio frequency ablation, cryoablation, ultrasound energy ablation, laser ablation and/or the like. Optionally, the ablation member may further include a partially retractable radio frequency coil, or other partially retractable apparatus for transmitting energy. In such embodiments, the method will further include deploying the retractable radio frequency coil or other apparatus to allow the ablation member to contact additional tissue. For example, such a retractable apparatus may be used with a U-shaped device to allow the ablation member to encircle or surround heart tissue around two pulmonary veins.

In yet other embodiments, the tissue stabilization/ablation device further includes at least one sensor for sensing ablation of the tissue. In such embodiments, methods will include sensing, with the sensor, an amount of ablation of the tissue. This may be accomplished via one or more sensing devices, such as thermal sensors, electrocardiogram sensors, radio frequency sensors, or the like, positioned adjacent the ablation member. In some embodiments, sensors may be used to sense ablation occurring at different parts of the ablation member. Typically, but not in all embodiments, sensors will comprise pairs of sensor, with one sensor in each pair transmitting a signal across an area to be ablated and its paired sensor receiving the signal. Since ablated tissue will generally transmit signal poorly, the pairs of signals can detect which areas of tissue have been ablated.

Optionally, the tissue stabilization/ablation device may include at least one cooling member for decreasing heat generated by the ablation member. In such embodiments, methods will include cooling the tissue stabilizer using the cooling member. For example, the cooling member may include a hollow member through which a cooling fluid may be passed to cool an ablation member, adjacent tissue and/or the like. The hollow member may take the form of a tubular member, a bladder or the like. In other embodiments, a cooling member may comprise a series of fluid outlet ports for allowing cooling fluid to be passed through a portion of the device to be cooled.

In another aspect of the invention, a device for stabilizing and ablating tissue generally includes a flexible rigidifying bladder, a tissue securing bladder and at least one ablation member. The flexible bladder includes at least one chamber within the bladder, at least one port in communication with the chamber, and rigidifying structure disposed within the chamber, wherein evacuation of the chamber via the port causes the rigidifying bladder to rigidify. The tissue securing bladder is coupled with the flexible rigidifying bladder and is configured to contact the tissue and generate a suction force to enhance contact of the device with the tissue. Finally, the ablation member is coupled with the tissue securing bladder for ablating at least a portion of the tissue with which the tissue securing bladder is in contact.

Generally, the flexible rigidifying bladder, tissue securing bladder and ablation member(s) may have any suitable shape, size or configuration, in two or three dimensions, for stabilizing and ablating tissue. For example, in some embodiments the tissue securing bladder comprises a flat U-shaped bladder for contacting heart tissue adjacent at least two pulmonary veins. The ablation member may also be a U-shaped member for ablating tissue adjacent at least two pulmonary veins. In another embodiment, the tissue securing bladder may comprise a conically-shaped, elliptically-shaped or pyramidally-shaped member.

Typically, the tissue securing bladder includes at least one suction hole for applying suction to enhance the contact of the bladder to the tissue. In some embodiments, the suction hole is configured to allow a portion of the tissue to be drawn into the hole when suction is applied. The ablation member may then be disposed about the at least one suction hole, to allow ablation of the portion of tissue drawn into the suction hole.

Generally, the ablation member may have any suitable configuration. In some embodiments, for example, multiple ablation members may be used to ablate a desired pattern on a tissue. In one embodiment, for example, the ablation members include a first linear ablation member for contacting heart tissue between a left pulmonary vein and a right pulmonary vein; a second linear ablation member for contacting heart tissue at a location approximating a line extending to the atrioventricular groove of a heart, and a third linear ablation member for contacting heart tissue on a left atrial appendage. In another embodiment, ablation member is configured to ablate tissue adjacent at least one pulmonary vein. This tissue may include epicardial tissue wholly or partially surrounding or encircling two pulmonary veins, for example. Any pattern of ablation is contemplated within the scope of the present invention.

Typically, the ablation member comprises an energy transmission member. The transmitted energy may be radio frequency energy, ultrasound energy, microwave energy, cryogenic energy or any other form of energy suitable for ablation. For example, one or more radio frequency coils are often used as an ablation member. In other embodiments, however, thermoelectric chips may be used. In general, any suitable energy transmission device may be used as ablation members in the present invention.

Optionally, as mentioned above, the device may include one or more sensors for sensing ablation of the tissue. In some embodiments, for example, such sensors sense an electrical depolarization in heart tissue. The sensors may generally include thermal sensors, electrical sensors, thermoelectric sensors, microchips, ultrasound sensors and/or the like. In some embodiments, pairs of sensors may be positioned on opposite sides of an ablation member to sense activity of the ablation member. In each pair, one sensor may send a signal toward an a second sensor across an area of ablated tissue. Since a given form of energy may not travel across ablated tissue, the pair of sensors will detect effective ablation when the energy is not transmitted across the tissue.

Also as mentioned above, devices of the present invention may include at least one cooling member for decreasing heat generated by the ablation member. For example, the cooling member may include a hollow tubular member adjacent the ablation member and at least one port coupled with the hollow member for allowing introduction of one or more cooling fluids into the hollow member. Some embodiments include an inlet port for allowing the introduction of one or more cooling fluids and an outlet port for allowing egress of the one or more cooling fluids from the hollow tubular member.

Devices of the present invention may be introduced to an area for treatment and may be positioned by any suitable means. For example, devices of the invention will typically include one or more positioning devices coupled with the rigidifying bladder and/or the tissue securing bladder. A positioning device may include a plate or foot, which may be coupled with an arm to position the device. Such a plate or foot may be positioned between the bladders, outside the bladders or at any other suitable location. In some embodiments, devices will be sufficiently flexible to be rolled up and inserted to a treatment site via a trocar. In such embodiments, positioning members may be disposed on the outside of one of the bladders such that the positioning members are couplable with a positioning arm or similar device.

In another aspect of the present invention, a device for stabilizing and ablating tissue includes a flexible rigidifying bladder and at least one ablation member coupled with the flexible rigidifying bladder for ablating at least a portion of the tissue. The flexible bladder includes a chamber, at least one port in communication with the chamber, at least one tissue securing means in communication with the chamber, at least one mesh-like member for dividing the chamber into multiple sub-chambers, and rigidifying structure disposed within at least one sub-chamber. In this embodiment, application of suction to the chamber via the port causes the rigidifying structure to rigidify the bladder and causes the tissue securing means to adhere to the tissue. In some embodiments, the tissue securing means comprises one or more suction members. Generally, any of the variations and optional features described above may be applied to this embodiment of the invention.

It should be understood that devices and methods of the present invention may suitably include any additional apparatus to enhance minimally invasive tissue stabilization and ablation. For example, devices may include one or more endoscopic devices for enhancing visualization, one or more elongate shafts or other positioning arms for placing a device, one or more trocar sheaths for introducing a flexible device and/or the like. All such embodiments and variations are contemplated within the scope of the invention.

BRIEF DESCRIPTION OF THE DRAWINGS

FIG. 3A' is view similar to that of FIG. 3A, illustrating the rigidifying bladder with applied suction.

DETAILED DESCRIPTION OF THE INVENTION

Devices and methods of the present invention generally provide for stabilization and ablation of a body tissue. Various embodiments are often described below in the context of stabilizing and ablating epicardial tissue on a human heart in proximity to one or more pulmonary veins for treating atrial fibrillation. It should be understood, however, that these or other embodiments may be used for stabilization and/or ablation of any other suitable human body tissues, may be used in a veterinary, research or other context, may be employed to treat a wide variety of other conditions, and/or the like, without departing from the scope of the present invention.

Typically, devices of the present invention include a rigidifying tissue stabilization device coupled with one or more ablation members. For example, a tissue stabilization device may include a rigidifying bladder coupled with a tissue securing bladder. Some embodiments also include additional features, such as but not limited to sensing members, cooling members and/or engaging members for coupling the device with a positioner. Methods generally provide for contacting a device with a tissue, stabilizing the tissue with the device and ablating the tissue. In various embodiments, tissue may be contacted and ablated in any suitable pattern, configuration and/or geometry and with any suitable type or power of ablation device. Although specific exemplary devices and methods are described in detail below and in the appended drawing figures, these examples are intended for illustrative purposes only and should not limit the scope of the invention as set forth in the claims.

Referring now to FIGS. 1 and 2A-E, a cardiac stabilization and ablation device 10 according to one embodiment of the present invention is shown. One example of an apparatus for stabilizing tissue is described in U.S. Pat. No. 6,251,065, issued to Kochamba et al., of which the present application is a continuation-in-part.

Figure 1:
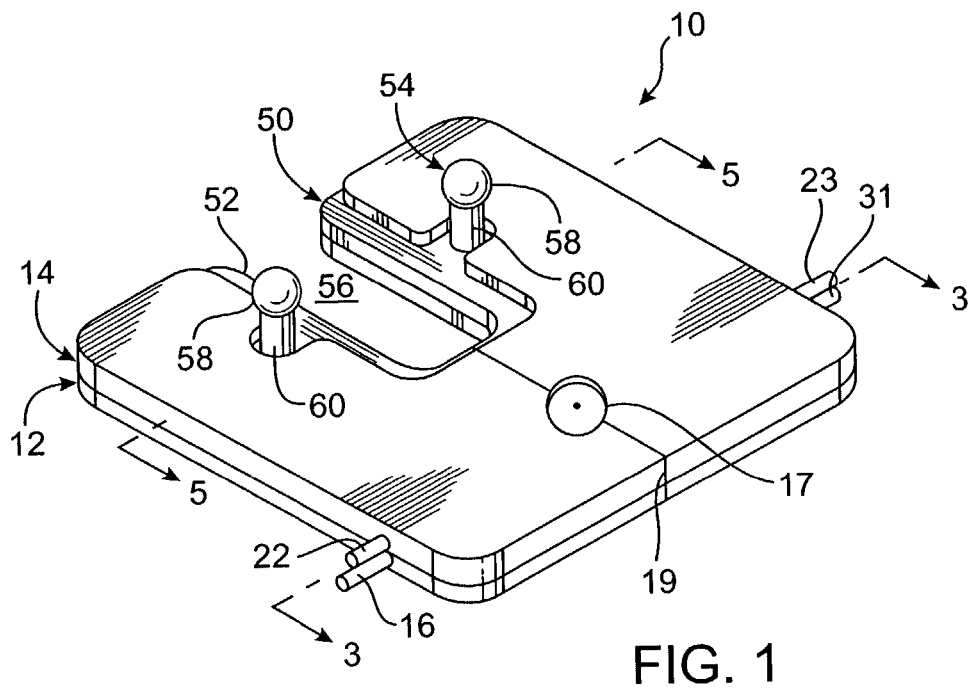
FIG. 1 is a perspective, top-surface view of an exemplary cardiac stabilization and ablation device in accordance with one embodiment of the present invention.

FIG. 1 is a top, or superior perspective, view of stabilization/ablation device 10, many features of which are described more fully below and/or in U.S. Pat. No. 6,251, 065. Generally, stabilization/ablation device 10 includes a tissue attaching bladder 12 for contacting device 10 with a body tissue, a rigidifying bladder 14 coupled with tissue attaching bladder 12, and an ablation member 13 (FIGS. 2A-E) coupled with tissue attaching bladder 12 for ablating the body tissue. These elements are described in further detail below.

Many embodiments of device 10 also include one or more engaging members for enabling the device to be removably coupled with a positioning device and/or for enhancing the contact of device 10 with a tissue to be ablated. For example, some embodiments include a rigid plate 52 coupled with one or more engaging structures 54 for engaging with a positioning arm or other positioning device. In FIG. 1, for example, engaging structure 54 includes a post 60 and a ball 58 coupled with one end of the post. As described further below, other embodiments do not include a rigid plate, allowing device 10 to be predominantly flexible when not in its rigidified state. Such a flexible device 10 may be manipulated, such as by folding, to enable the device to be introduced to a surgical site via a minimally invasive introducer or similar means. These optional elements are described in more detail below.

It should be emphasized that although shown as a U-shaped, relatively flat device in FIGS. 1, 2A-E and many of the following figures, device 10 may have any suitable shape, size and configuration, in two or three dimensions, for stabilizing and ablating tissue. In various embodiments, for example, device 10 may be round, square, ovoid, curved, circular, cylindrical, linear, elongate, conical or the like. Additionally, attaching bladder 12 may have a different size or shape than rigidifying bladder 14 in some embodiments. In fact, attaching bladder 12, rigidifying bladder 14 and ablation member 13 may be given any suitable shapes, sizes or combination of shapes and sizes, without departing from the scope of the present invention.

In some embodiments, as shown in FIG. 1, device 10 further includes one or more hinges 19, each with or without a hinge actuation member 17. Hinge 19 may allow the shape of device 10 to be adjusted, for example to conform to a desired ablation pattern at a treatment site. Actuation member 17 may be used to activate or loosen hinge 19. For example, device 10 may be adjusted via hinge to close the open portion at the top of the U of device 10, such as when it desired to ablate tissue encircling a structure. In other embodiments, two or more hinges 19 may be disposed on device 10 at various locations to allow further adjustment of device 10. Just as with device 10 as a whole, hinges 19 on and adjustments to device 10 may assume any suitable configuration.

Figure 2A:
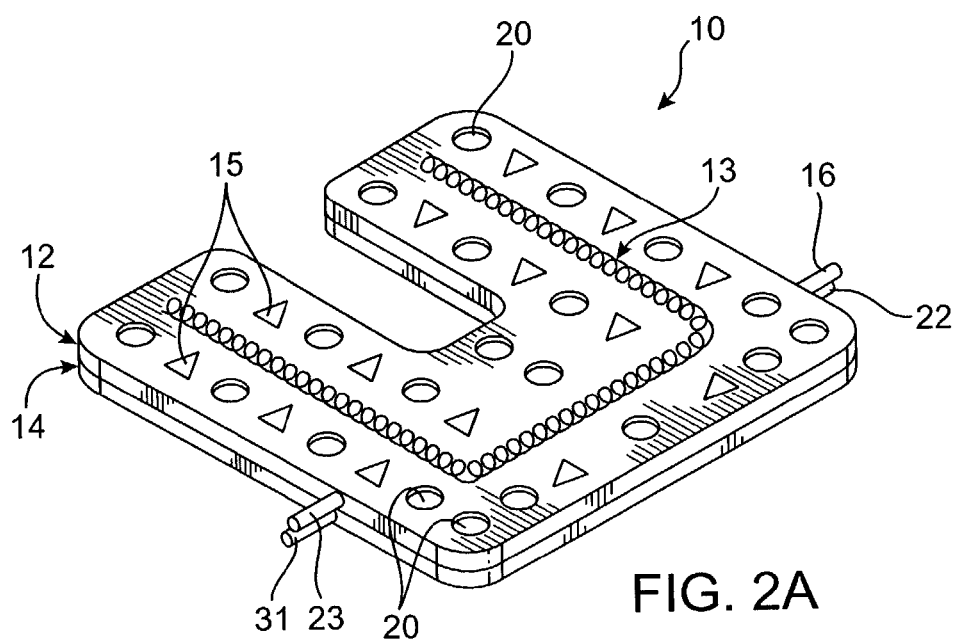
FIGS. 2A-E are perspective, bottom-surface views of various embodiments of a cardiac stabilization and ablation device as in FIG. 1.

Referring now to FIG. 2A, a bottom, or inferior perspective, of device 10 is shown. Typically, one or more ablation members 13 and one or more sensors 15 are coupled with tissue attaching bladder 12 to enable ablation of tissue contacted with attaching bladder 12 and sensing of ablation by sensors 15. In some embodiments, ablation member 13 and sensors 15 are positioned on the surface of attaching bladder 12, while in other embodiments they may be embedded in attaching bladder 12 or otherwise coupled therewith.

In many embodiments, stabilization/ablation device 10 is largely flexible and conformable to the shape or anatomical topography of a particular piece or section of tissue, such as the epicardium of the left or right ventricle or left or right atria of a heart. Thus, ablation device 10 may be flexibly placed in contact with a tissue surface in a substantially atraumatic manner and then secured to the tissue via tissue attaching bladder 12, for example through the use of suction. Once ablation device 10 is conformed and secured to a tissue surface, it may then be rigidified via rigidifying bladder 14 to maintain a desired shape. In some embodiments, for example, rigidifying bladder 14 may actuated by applying suction. Once ablation device 10 is in place on a tissue, ablation member 13 may be activated to ablate the tissue. Each of these features of the present invention will be described in detail below.

Ablation member 13 is generally configured for conveying ablative energy from an energy source to a tissue. In various embodiments, such ablative energy may include radio frequency (RF) energy, ultrasonic energy, microwave energy, cryoablative energy, or any other suitable source of energy. In some embodiments, in fact, ablation member 13 may include an apparatus for delivering one or more ablative drugs or other chemical compounds to a tissue. Therefore, although much of the following description focuses on an embodiment including an RF coil ablation member 13, this example should not be interpreted to narrow the scope of the invention in any way. Any suitable source of energy for ablation member 13 may be used.

Furthermore, ablation member 13 may have any suitable configuration, shape or the like. In some embodiments, as in FIG. 2A, ablation member 13 is a single U-shaped RF coil. In other embodiments, ablation member 13 comprises more than one coil or other ablation device. For example, in one embodiment ablation member 13 may include one or more RF coils, each formed in a straight, curved, or shaped line. Multiple coils may be used to ablate various patterns on various tissue surfaces, such as when creating various patterns on epicardial surfaces of hearts to treat AF. In an embodiment shown in FIG. 2E, for example, three linear RF coils may be used to ablate epicardial tissue. A first coil 92 ablates in a line running between a left pulmonary vein and a right pulmonary vein, a second coil 94 ablates in a line extending to the atrioventricular groove of the heart, and a third coil 96 ablates in a line extending to the left atrial appendage. As demonstrated by this embodiment, two or more coils or other ablation members may overlap. In other embodiments, linear coils may be used to extend ablation patterns to the right side of the heart, to the coronary sinus, to the superior or inferior vena cava, to the tricuspid valve annulus, to the right atrial appendage, and/or the like. In another embodiment, linear coils may be used in addition to RF coils which partially or wholly surround the pulmonary veins on one or more sides of the heart. In another embodiment, ablation member 13 has a circular configuration to ablate in a pattern around a structure.

Other energy sources may be used for ablation. For example, as shown in FIG. 2D, multiple thermoelectric chips 82 may be used as ablation members 13 to transmit cryogenic energy. Such chips 82 may be arranged, for example, in a series or array to ablate tissue in a desired pattern.

Figure 2B:
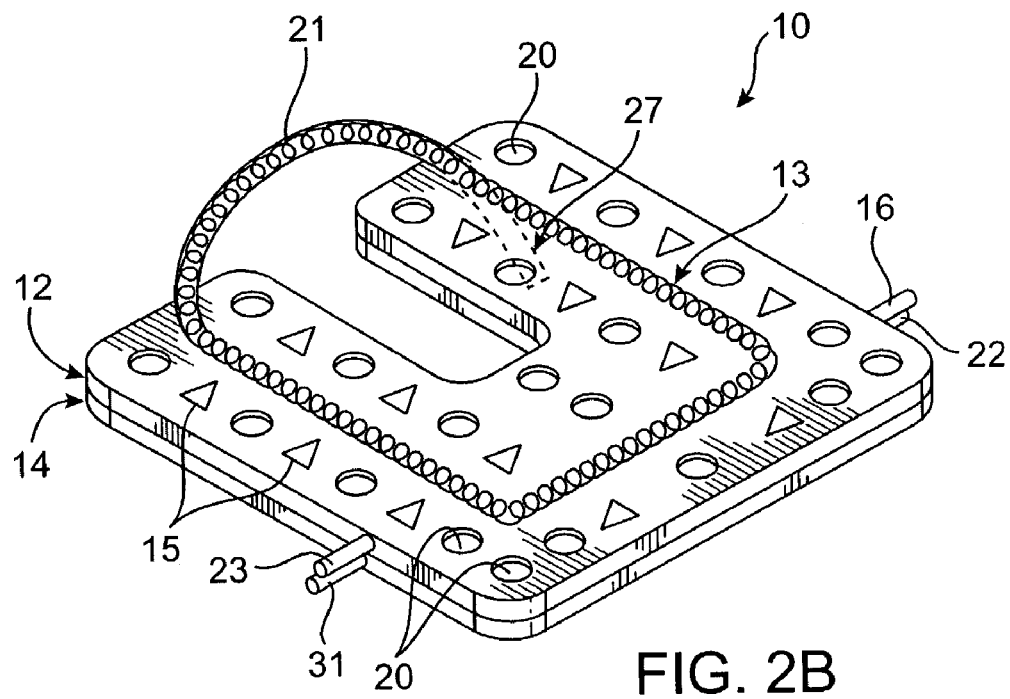

Referring now to FIG. 2B, ablation member 13 may also include a retractable coil 21. Retractable coil 21 may be retracted into a coil housing 27 and may be released by activation of a button or other releasing device (not shown). In some embodiments, for example as in FIG. 2B, such retractable coil 21 may be released to cross the open end of a U-shaped ablation/stabilization device 10. This would allow for ablation in a pattern encircling one or more structures. For example, tissue may be ablated in a pattern encircling one or more pulmonary veins using such an embodiment.

It should be apparent that many configurations, dimensions, shapes and combinations of ablation apparatus may be incorporated into ablation member 13 without departing from the scope of the present invention. For example, in one embodiment, ablation member 13 may be formed in a U-shaped, semicircular, circular, or similar configuration to ablate an epicardial area adjacent to and/or around one or more pulmonary veins on a heart. In one embodiment of a U-shaped, RF coil ablation member 13, the depth of the internal surface of the U may measure between about 2.5 and about 5.0 inches, and more preferably between about 3.0 and about 4.0 inches, and the width of the internal surface of the U may measure between about 0.25 and about 2.0 inches, and more preferably between about 0.5 and about 1.5 inches.

Figure 2C:
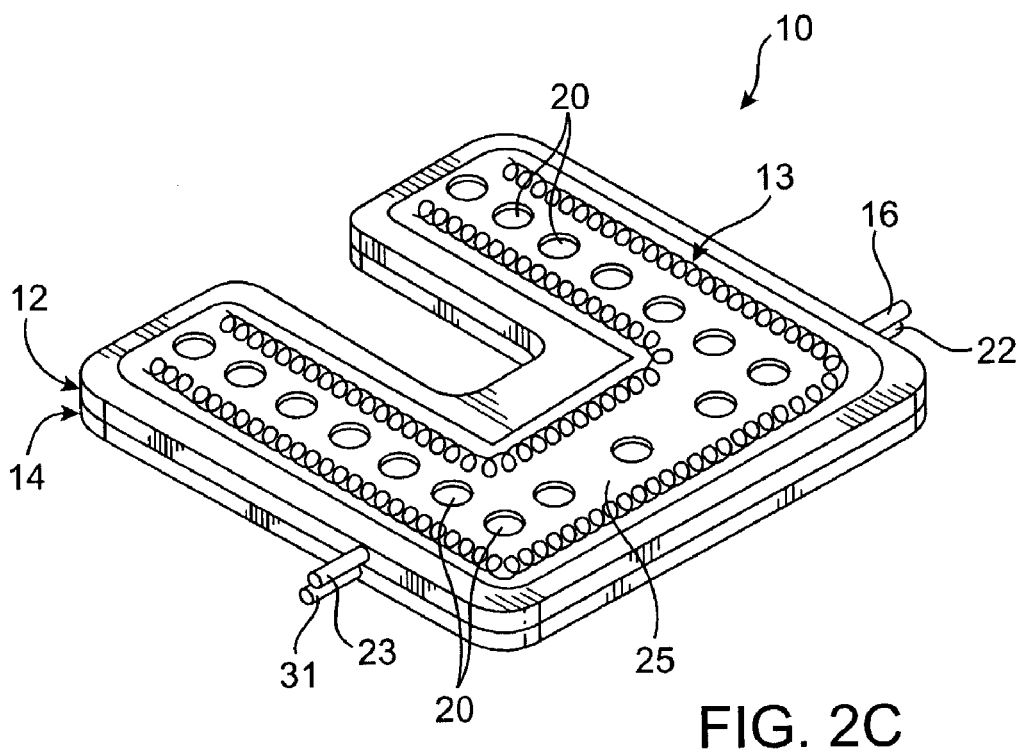
Figure 2D:
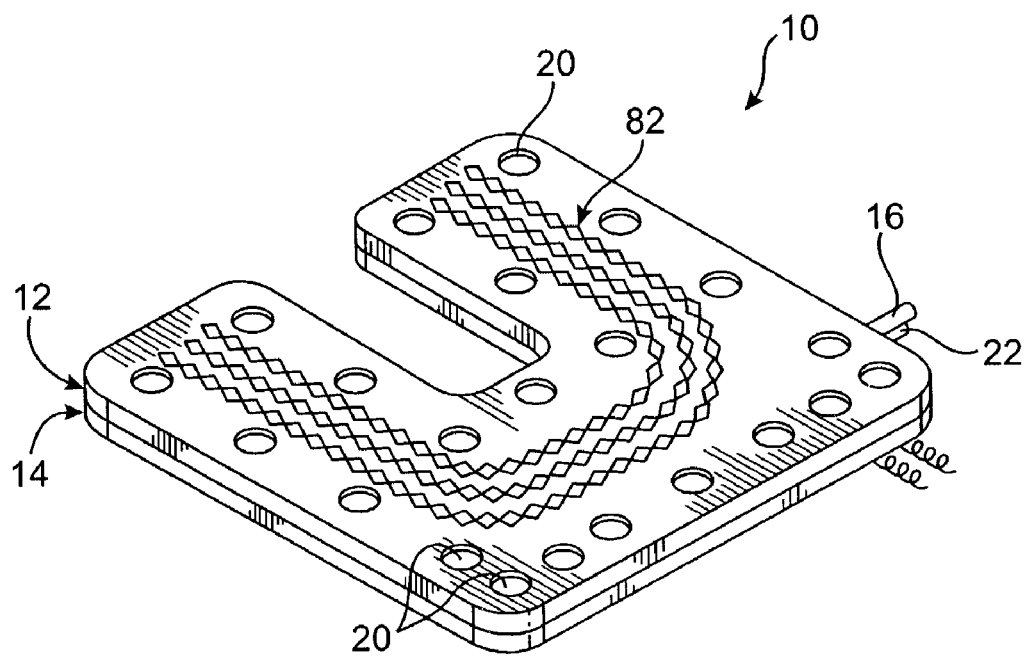
Figure 2E:
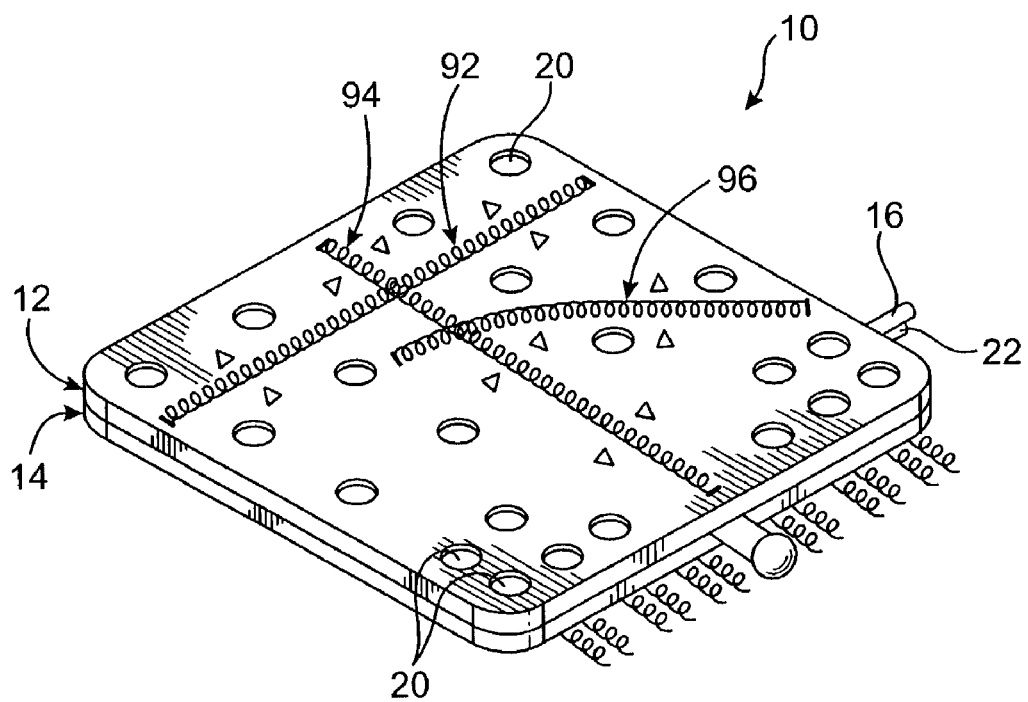

With reference now to FIG. 2C, in yet another embodiment of ablation/stabilization device 10, ablation member 13 may be configured as a bipolar RF device. As shown in FIG. 2c, such a bipolar ablation member 13 typically includes two ablation members 13. These bipolar ablation members 13 may be aligned towards the internal and external curvatures of a U-shaped device 10 or in any other suitable configuration to provide bipolar ablation.

As stated briefly above, ablation member 13 as in any of the embodiments shown in FIGS. 2A-C and/or described above may use any suitable energy source and may be coupled with an energy source in any suitable manner. Thus, energy used to ablate tissue may include, but is not limited to, RF, microwave, ultrasound and cryogenic energy. Connection apparatus and energy sources are not shown in the drawing figures, but it will be apparent to those skilled in the art that any suitable energy source may be coupled with device 10 by any suitable means. Additionally, in various embodiments energy source may be external and coupled via wiring, internal to device 10, external and coupled remotely, or configured in any other suitable way to provide energy to device 10.

Various embodiments of stabilization/ablation device 10 may further include one or more cooling members for cooling ablation member 13, other portions of device 10 and/or contacted tissue. For clarity, such cooling members are not shown in the drawing figures. However, a coolant inlet port 23 and coolant outlet port 31 are shown in FIGS. 2A-C. Many embodiments of device 10 include one or more cooling members and most of those embodiments use one or more coolant fluids to achieve cooling of ablation member 13. The cooling member (or members), for example, may include a hollow apparatus positioned in close proximity to ablation member 13, either on one side or on both sides of ablation member 13. The hollow apparatus may comprise, for example, a tubular member, a bladder or the like. A cooling fluid, such as saline, water, or other suitable fluid may be infused into the hollow apparatus via coolant inlet port 23, allowed to circulate through the hollow cooling member and then allowed to exit the cooling member via coolant outlet port 31.

Other embodiments may use multiple irrigation or outlet ports to cool ablated tissue and/or device 10. Outlet ports may comprise multiple small holes in device 10, disposed around an ablation member or in any other suitable configuration, allowing fluid to be passed through the holes to cool tissue or the device itself. Providing circulation of a cooling fluid in close proximity to ablation member 13 in such a manner will typically decrease both the impedance and the temperature of ablation member 13 to increase efficiency and prevent unwanted overheating. Generally, cooling members may have any suitable shapes, sizes and configurations and may use any suitable means for cooling. For example, some cooling members may encircle ablation member 10, some may use coolants or cooling mechanisms other than circulation of a fluid, and/or the like.

Referring to FIGS. 2A-B, various embodiments of ablation device 10 may include one or more sensors 15 for sensing ablation by ablation member 13. For example, sensors 15 may measure heat generated by ablation member 13, may sense heat delivered to a contacted tissue, may sense electrical or other energy potentials, and/or may use any other suitable means for sensing ablation. In some embodiments, for example, sensors 15 detect RF current, impedance and/or the like. Sensors 15 may be positioned in pairs, each member of a pair being positioned on opposite sides of ablation member 13. RF energy may be transmitted to different portions of ablation member 13 through different RF channels and a pair of sensors 15 may accompany each different portion of ablation member 13. Each pair of sensors 15 may then measure ablation from a portion of ablation member 13 and measurements from pairs of sensors 15 can be compared to determine whether certain portions of ablation member 13 are ablating at a higher current, have a higher impedance, and/or the like, compared to other portions of ablating member 13. In such an embodiment, one sensor from each pair of sensors 15 may send a signal to its accompanying sensor across ablation member 13 and its accompanying sensor 15 may act as a receiver. Transmitted energy from a sending sensor 15 may not typically reach its paired sensor 15 across ablated tissue, since ablated tissue will not typically transmit energy efficiently. Thus, a pair of sensors 15 may detect ablation in tissue. Sent and received signals may be processed by a microprocessor (not shown), which may either be built into device 10 or be disposed apart from device 10.

It should be apparent that any type, combination or configuration of sensors may be used to sense ablation in device 10. Thus, individual sensors 15 rather than pairs are contemplated, as well as sensors distributed in any suitable pattern in or on device 10. Furthermore, any type of apparatus suitable for sensing transmission of energy may be used. Therefore, sensors 15 of the present invention are not limited to the pairs of RF sensors described above. Additionally, any suitable means for sending and receiving signals to and from sensors 15 may be used. In one embodiment, for example, a microprocessor chip is embedded within device to send and receive signals to and from sensors 15. In other embodiments, sensors 15 may each separately send and receive signals to a microprocessor separate from device.

Referring now to FIG. 2C, yet another embodiment of stabilization/ablation device 10 includes one or more tissue ports 25. Tissue port 25 is generally a concavity or trough of any shape, including for example a conical shape, on the surface of attaching bladder 12 which may or may not extend into a concavity on rigidifying bladder 14. In one embodiment, one or more tissue port 25 may be configured to draw tissue toward suction openings 20 disposed within port 25. One or more components of device 10 described above and below, such as ablation member 13, sensors 15, cooling members, suctioning devices and/or the like may be positioned in tissue ports 25. Generally, placing one or more concave tissue ports 25 on attaching member 12 may enhance attachment of attaching member 12, and therefore of device 10, to tissue. Tissue ports 25 may thus enhance efficiency of stabilization and/or ablation by device 10.

Figure 3A:
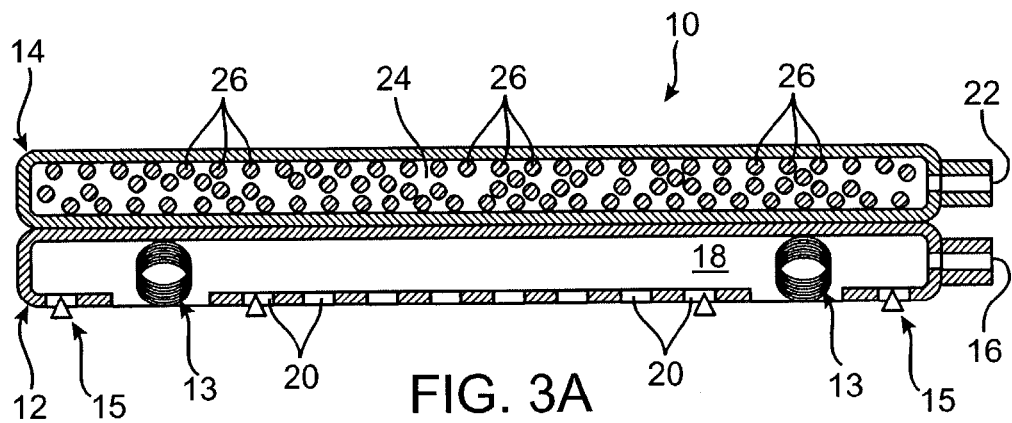
FIG. 3A is a cross-sectional view of the stabilization componentcardiac stabilization and ablation device taken along line 3-3 of FIG. 1, illustrating a rigidifying bladder without applied suction.
Figure 3A:
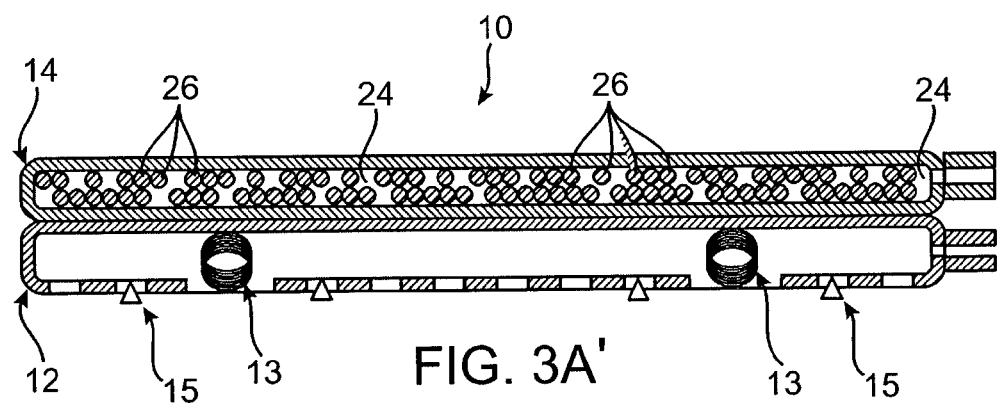

With reference to FIG. 3A, attaching bladder 12 and rigidifying bladder 14 are shown in cross section. In one embodiment, attaching bladder 12 has a port 16 leading into an inner chamber 18 in which a plurality of openings 20 are formed. Attaching bladder 12 is substantially flexible and configured so that openings 20 apply suction when suction is applied at port 16. Rigidifying bladder 14 has a port 22 leading into an inner chamber 24 in which rigidifying structure 26 is disposed. A portion of rigidifying structure 26 may be attached to bladder 14, and a portion of the rigidifying structure may be unattached or free floating. Free-floating rigidifying structure is exemplified in the figures by substantially spherical beads or balls, although any structure configured in accordance with the principles of the present invention may be utilized. In addition, rigidifying structure 26 may be configured as a mesh-like sheet or as a corrugated sheet of material made from, for example, nylon implanted or impregnated with silicone. At least a portion of the mesh-like or corrugated sheet may be attached to rigidifying bladder 14. (The dimensions of the components of stabilization/ablation device 10 in the drawings, such as the thickness of the walls of bladders 12 and 14 are exaggerated for illustrative purposes.)

With reference to FIGS. 3A and 3A', rigidifying bladder 14 is configured to be substantially flexible when suction is not applied at port 22, which is shown in FIG. 3A, and substantially rigid when suction is applied at port 22, which is shown in FIG. 3A'. As shown in FIG. 3A, inner chamber 24 has an ambient volume which provides space in which portions of rigidifying structure 26 may move with respect to each other, allowing bladder 14 to bend and flex. However, when suction is applied at port 22, negative pressure or a vacuum is induced within inner chamber 24, causing rigidifying bladder 14 to collapse upon itself, as shown in FIG. 3A'. Inner chamber 24 now has a collapsed volume which is less than the ambient volume, and the space among rigidifying structure 26 is substantially reduced, thereby increasing the density of the rigidifying structure. Accordingly, individual portions of rigidifying structure 26 are urged together under pneumatic force and resist relative movement with respect to each other. As shown in the drawings, structures such as free-floating beads engage with spaces formed between attached beads to resist lateral movement relative to each other. If rigidifying structure 26 is configured as a mesh, then free-floating beans partially lodge within openings in the mesh. With the individual portions of rigidifying structure 26 urged together under vacuum to resist relative movement, collapsed rigidifying bladder 14 is substantially inflexible, resists bending, and retains a stiffened position.

Rigidifying bladder 14 may be manufactured using any suitable material or combination of materials. In one embodiment, for example, rigidifying bladder 14 may be comprised of silicone impregnated with nylon. Rigidifying bladder 14 may be include natural fibers such as cotton (e.g., canvas) or metallic fibers such as stainless-steel mesh to provide durability. Alternatively, rigidifying bladder 14 or other components of device 10 may be made from substantially resilient material, such as certain silicones, so as to stretch under sufficient force. In addition, rather than pneumatic evacuation of rigidifying bladder 14, fluids other than air, such as hydraulics may be used.

In this regard, a surgeon may apply and conform stabilization/ablation device 10 to tissue so that preferably a majority of openings 20 contact or are incident on the tissue. Suction may be applied at port 16, causing suction to be applied at the openings 20 and thereby attaching stabilization/ablation device 10 to the tissue. Suction may then be applied at port 22 to stiffen or rigidify device 10, causing the device to maintain a desired position and configuration on the tissue. In applying device 10 to tissue in this matter, the surgeon may manipulate the tissue as desired by manipulating the device because the tissue is held or secured by device 10. Accordingly, the secured tissue moves when device 10 moves or maintains a stabilized position when device 10 is motionless or anchored.

Figure 3B:
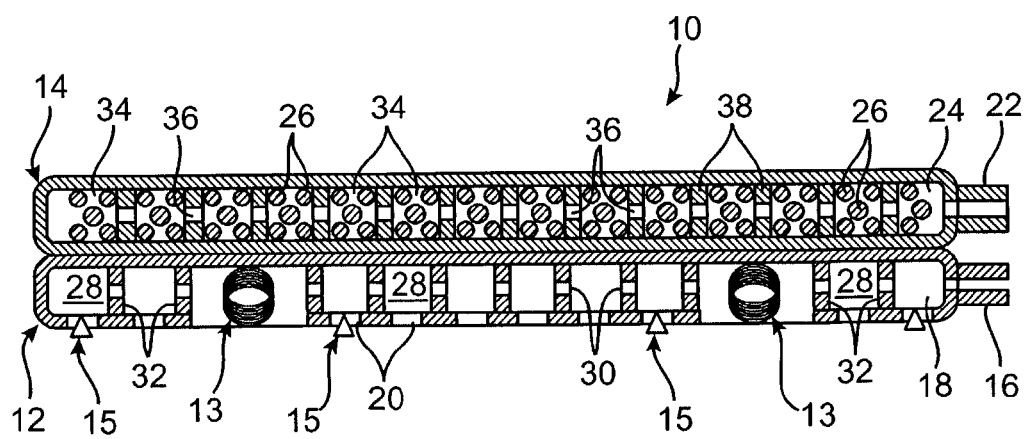
FIG. 3B is a cross-sectional view of the cardiac stabilization and ablation device taken along line 3-3 of FIG. 1, illustrating an alternative embodiment of the stabilizer.

An alternative embodiment of device 10 is illustrated in FIG. 3B. In this embodiment, tissue attaching bladder 12 is configured so that inner chamber 18 is divided into a plurality of cells 28 which are connected by a plurality of air passages 30 formed through dividing walls 32. Each cell 28 may be elongate in shape, extending substantially from one side of attaching bladder 12 to the other. Accordingly, each cell 28 may include a number of openings 20 disposed in a row along an extent thereof, such as illustrated in FIGS. 2a-c.

Also illustrated in FIG. 3B, rigidifying bladder 14 is configured so that inner chamber 24 is divided into a plurality of cells 34 which are connected by a plurality of air passages 36 formed through dividing walls 38. Each cell 34 of rigidifying bladder 14 may be elongate in shape, extending substantially from one side of bladder 14 to the other. Each cell 34 includes rigidifying structure 26 which may be disposed either attached to an inner wall of bladder 14 and/or dividing walls 38, free floating, or in a combination of both as shown in FIG. 3B. Free-floating rigidifying structure 26 may include spherical balls which are dimensioned to be larger than air passages 36 to prevent passage of the balls through passages 36, as shown in FIG. 3B.

Figure 3C:
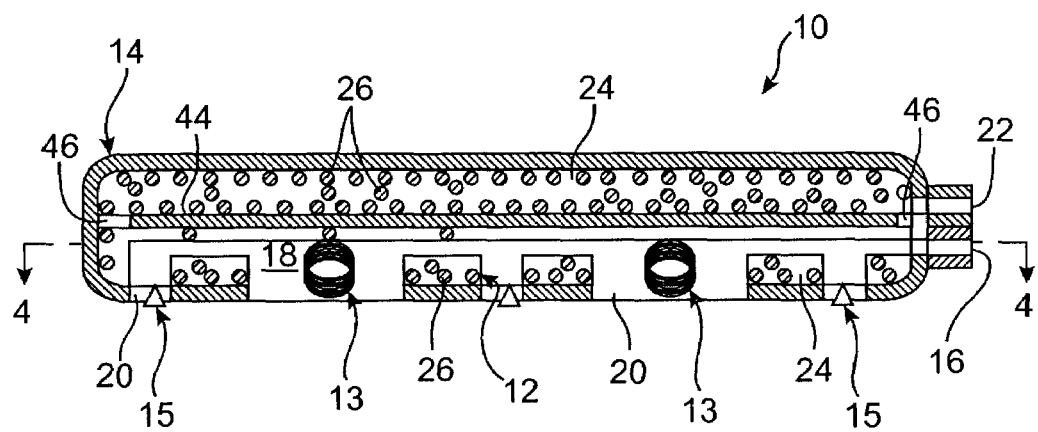
FIG. 3C is a cross-sectional view of the cardiac stabilization and ablation device taken along line 3-3 of FIG. 1, illustrating yet another alternative embodiment of the stabilizer.
Figure 4:
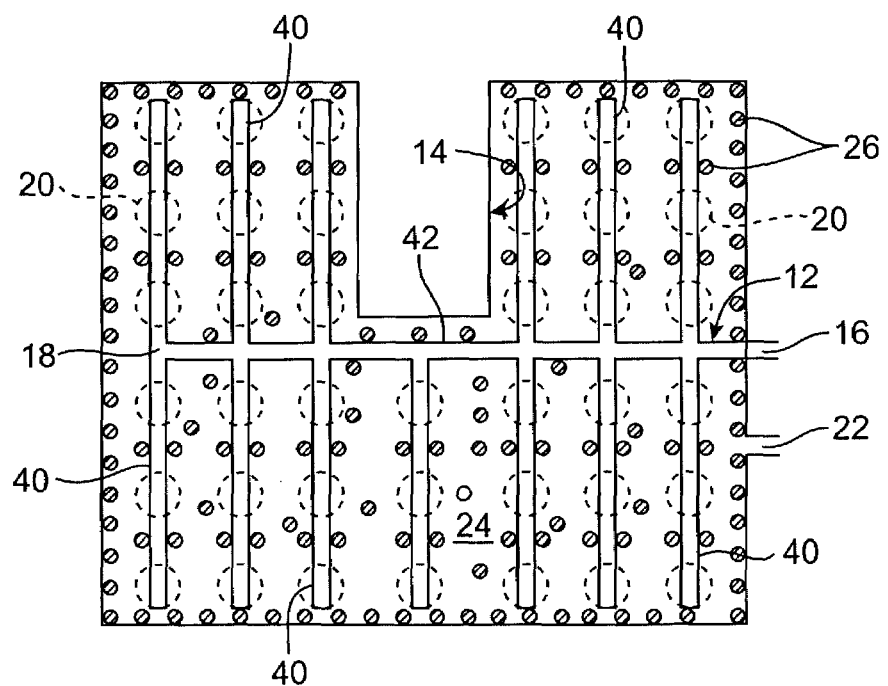
FIG. 4 is a cross-sectional view of the cardiac stabilization and ablation device taken along line 4-4 of FIG. 3C, without the ablation member shown.

Another alternative embodiment of the tissue stabilizer of the present invention is illustrated in FIGS. 3C and 4. Rather than attaching bladders 12 and 14 in a substantially coplanar and coextensive relationship as shown in FIGS. 3A and 3B, attaching bladder 12 is imbedded within rigidifying bladder 14 in device 10 shown in FIGS. 3C and 4. In this embodiment, attaching bladder 12 includes a plurality of branching arms 40 which extend from a central channel 42. Each arm 40 provides a pneumatic conduit to a number of the openings 20 of attaching bladder 12, thereby providing communication for each opening 20 to port 16 via the inner chamber 18. Rigidifying bladder 14 exemplified in FIGS. 3C and 4 may include an inner wall 44 which separates the inner chamber 24 into two layers or sections. Wall 44 includes at least one air passage 46 so that each section of chamber 24 is in pneumatic communication with port 22. Rigidifying structure 26 may include attached as well as free-floating structure analogous to that described above. Although a single inner wall 44 is illustrated, rigidifying bladder 14 may include a plurality of walls 44 to separate inner chamber 24 into a plurality of sections or layers.

With continued reference to FIGS. 3C and 4, one embodiment of the invention includes a combined bladder that has both rigidifying elements and tissue stabilizing elements. Such an embodiment, similar to that just described above, has one common chamber that is divided into one or more rigidifying sub-chambers and one or more tissue stabilizing sub-chambers by one or more pieces of mesh-like material. The mesh holds rigidifying structure within the rigidifying sub-chambers. All sub-chambers are in fluid communication, due to the mesh, so that when suction is applied at a common port (as if port 22 and port 16 were combined in FIG. 3C), the rigidifying sub-chambers rigidify and the tissue securing sub-chambers secure tissue. For example, the tissue securing sub-chambers may be in fluid communication with one or more suction holes for securing tissue.

Figure 5:
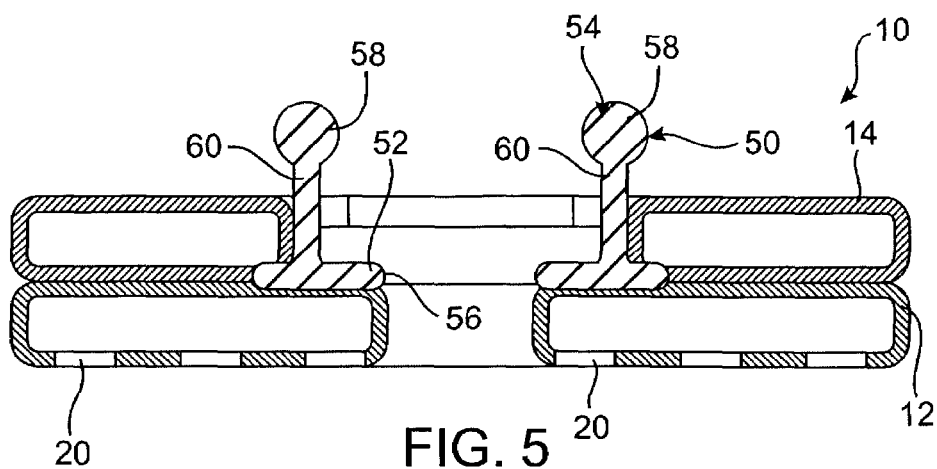
FIG. 5 is a cross-sectional view of the cardiac stabilization and ablation device taken along line 5-5 of FIG. 1, without the ablation member shown.

With reference now to FIGS. 1 and 5, stabilization/ablation device 10 of the present invention may also include a retaining structure 50 for engaging with external support apparatus. Retaining structure 50 may include one or more substantially rigid plates 52 and one or more engaging members 54. Plate 52 may be attached to either or both of bladders 12 or 14 with, for example, adhesive, suture or suture-like material, or any other suitable coupling apparatus. (Components of bladders 12 and 14 as described above are not shown in FIG. 5 for clarity.) Plate 52 may include a window 56 which provides a surgeon access to a surgical site on the tissue to which device 10 is attached. In the embodiment illustrated in the drawings, ablation device 10 and plate 52 have U-shape configurations, thereby defining window 56.

Although illustrated as a three-sided opening, window 56 may be four sided, that is, enclosed on all four sides. In addition, window 56 may be curvilinear (rather than rectilinear as shown) and may be offset from a medial axis of the tissue stabilizer (rather than centered as shown). Ablation device 10 may be configured so that window 56 is wider at a top surface of the device and narrower at a bottom surface of the device, or vice versa. In addition, multiple windows 56 may be formed in the tissue stabilizer. In a multiple window embodiment, windows 56 may function as a vent for promoting or facilitating air circulation, which will be discussed in reference to alternative embodiments of the invention described below. In other embodiments, no window may be included. For example, many embodiments of device may be used for predominantly ablation only procedures, so that surgeon access to tissue through a window in device 10 is not required.

Figure 5A:
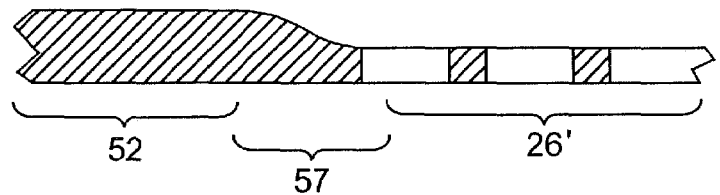
FIG. 5A is an enlarged fragmentary cross-sectional view of a rigid plate and rigidifying structure according to one embodiment of the invention.
Figure 5B:
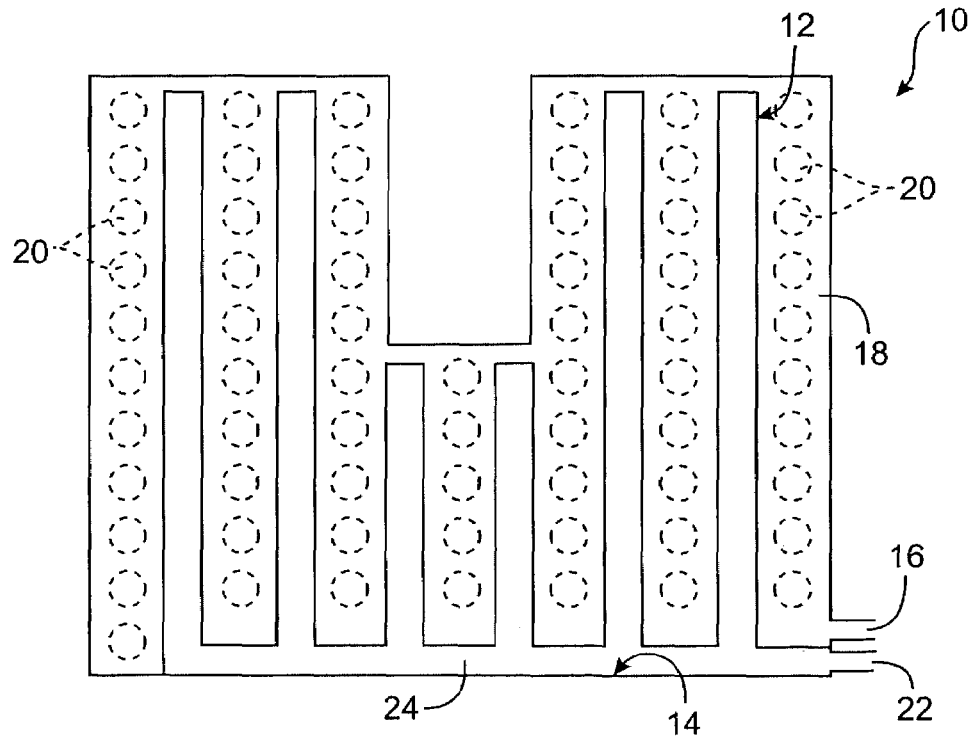
FIG. 5B is a cross-sectional view of a rigidifying structure according to one embodiment of the invention.

Referencing FIG. 5A, the junction of rigid plate 52 and the bladders (either or both of bladders 12 and 14) may be configured at a stress-reducing section 57. For example, rigidifying bladder 14 may include rigidifying structure 26' configured as a flexible nylon mesh, and plate 52 may be made from a substantially rigid nylon, with section 57 being defined as an integral transition therebetween. Stress-reducing section 57 is more resilient than rigid plate 52 but less resilient than mesh 26', thereby allowing the mesh to flex with respect to the plate.

Figure 6:
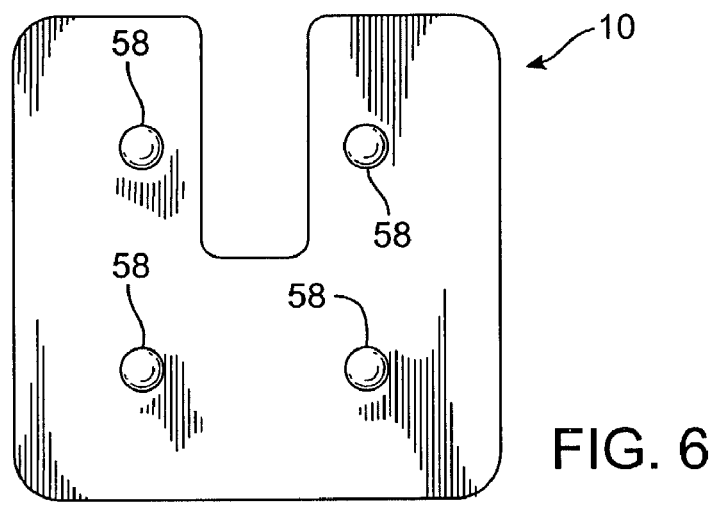
FIG. 6 is a plan view illustrating an exemplary embodiment of an engaging structure of the invention.

In various embodiments, engaging structure 54 may be configured as a ball 58 disposed on a post 60, with the post being attached to plate 52 and projecting away from bladders 12 and 14. As shown in the drawings, engaging structure 54 includes a pair of balls 58 and posts 60. Balls 58 are configured to releasably engage with complement external support structure, such as quick-release sockets with by a single flip lever operated with one hand as known in the art, which will be discussed in more detail below. Referring to FIG. 6, engaging structure 54 may include a plurality ball-and-post structures (58 and 60) arranged on tissue stabilizer 10. The plural balls 58 may be configured so that external support structure engages with at least two of the balls 58 simultaneously. As such, stabilization/ablation device 10 is retained in a substantially rigid manner in all dimensions.

Figure 7:
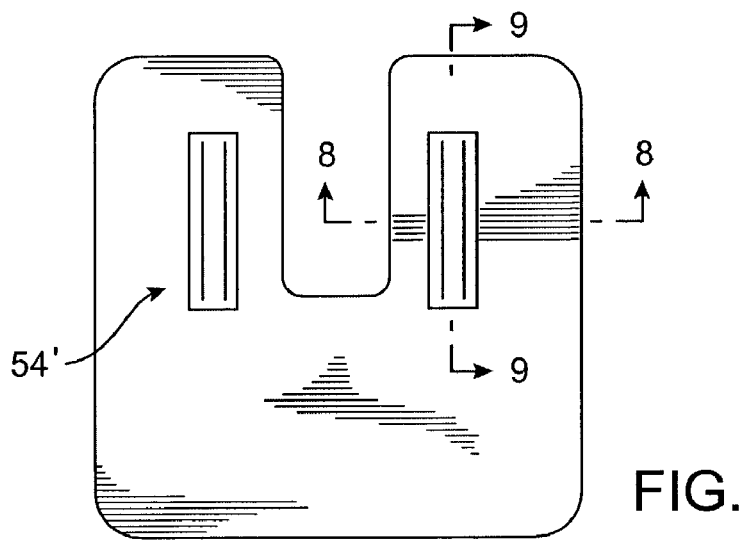
FIG. 7 is a plan view illustrating an alternative embodiment of an engaging structure of the invention.
Figures 8, 9:
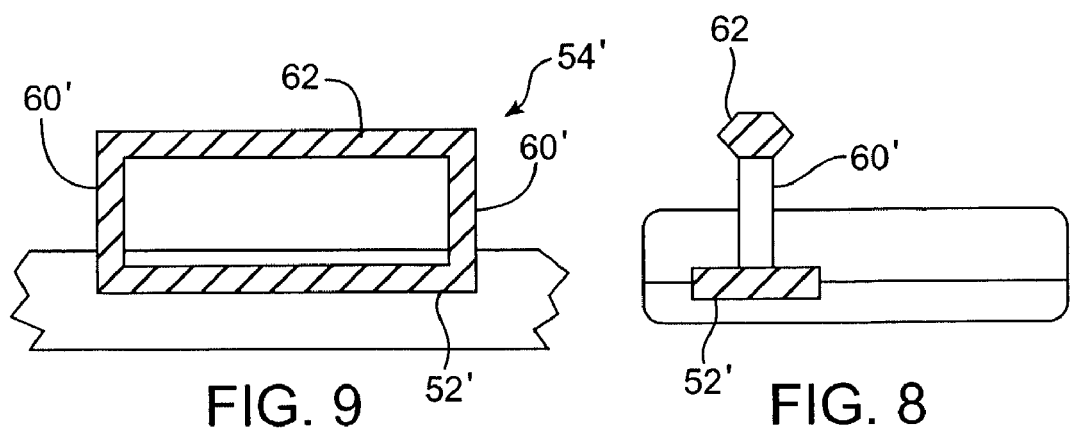
FIG. 8 is a cross-sectional view of the engaging structure taken along line 8-8 of FIG. 7.
FIG. 9 is a cross-sectional view of the engaging structure taken along line 9-9 of FIG. 7.

An alternative embodiment of the engaging structure of the present invention is illustrated in FIGS. 7, 8, and 9. Components of the alternative engaging structure 54' analogous to those shown in FIGS. 1 and 5 are referenced with like numerals with the addition of a prime ('). Exemplary engaging structure 54' may include a cross bar 62 extending between a respective pair of posts 60' connected to rigid plate 52'. As shown in the drawings, a pair of cross bars 62 may be used. Each cross bar 62 is substantially rigid and provides an extended structure to which external support apparatus may be easily attached. When attached, ablation device 10 is pivotal only about a single axis, that is, the axis of the cross bar which is engaged with external structure. As particularly shown in FIG. 8, each cross bar 62 may have a polygonal cross section, for example, a hexagon.

Still further embodiments of retaining structures 50 of the present invention are shown in FIGS. 12A-B and 13A-B.

Figure 11:
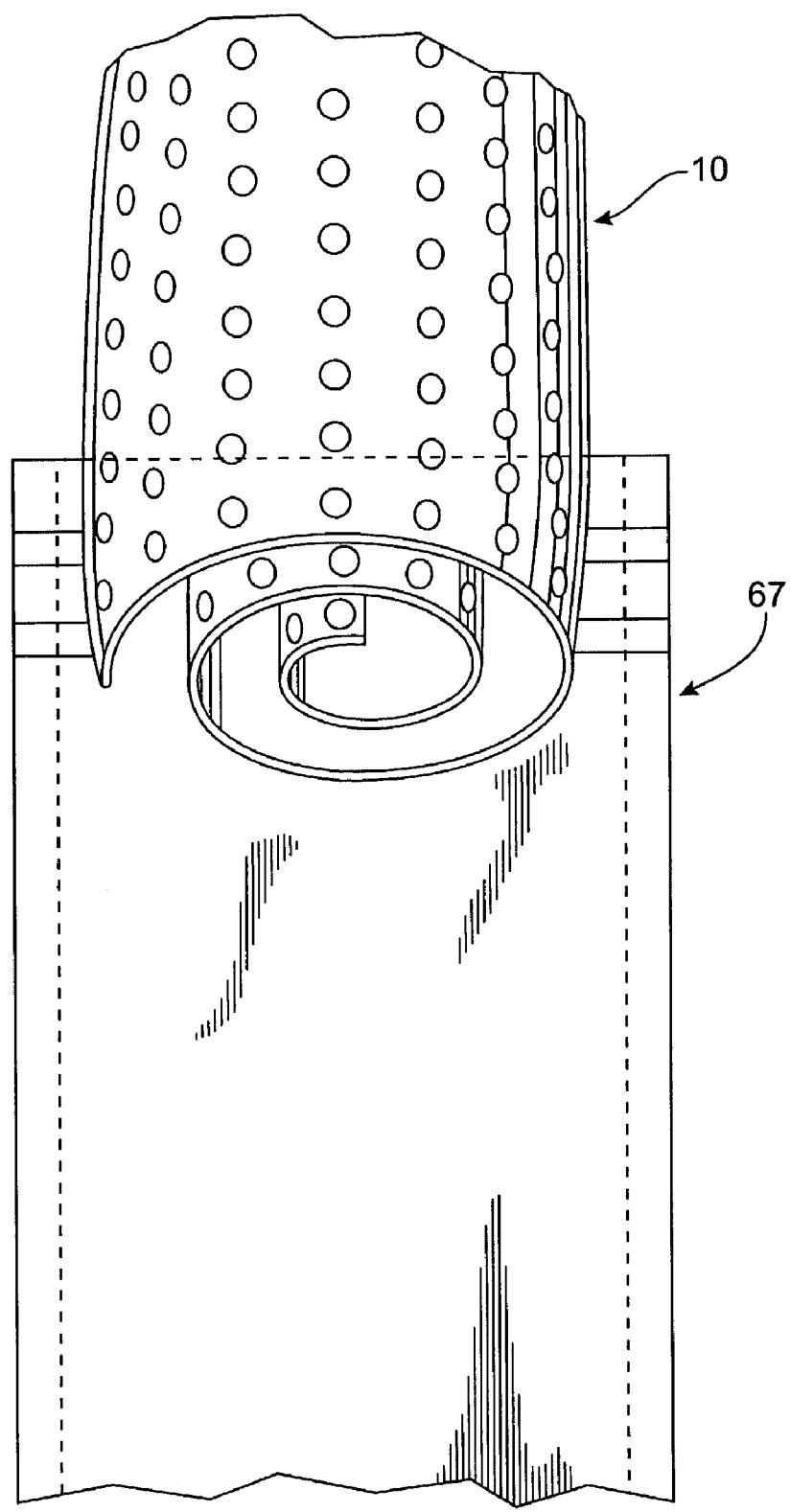
FIG. 11 is a perspective view of an embodiment of a cardiac stabilization and ablation device of the present invention which may be inserted into a body through a trocar sheath.
Figure 12A:
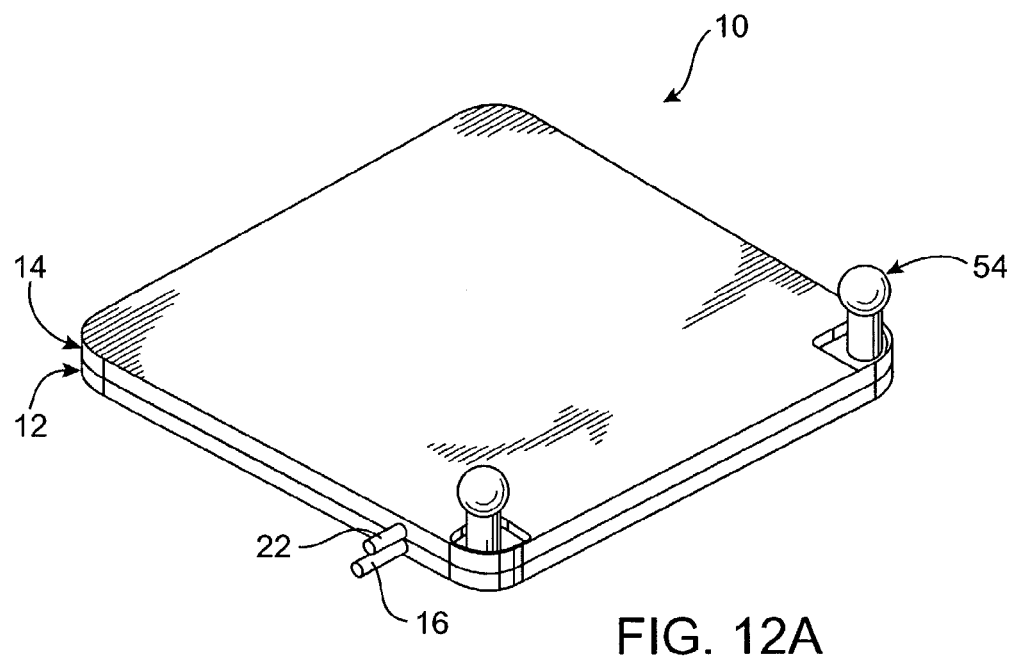
FIG. 12A is a perspective view of another embodiment of a cardiac stabilization and ablation device of the present invention which may be inserted into a body through a trocar sheath.
Figure 12B:
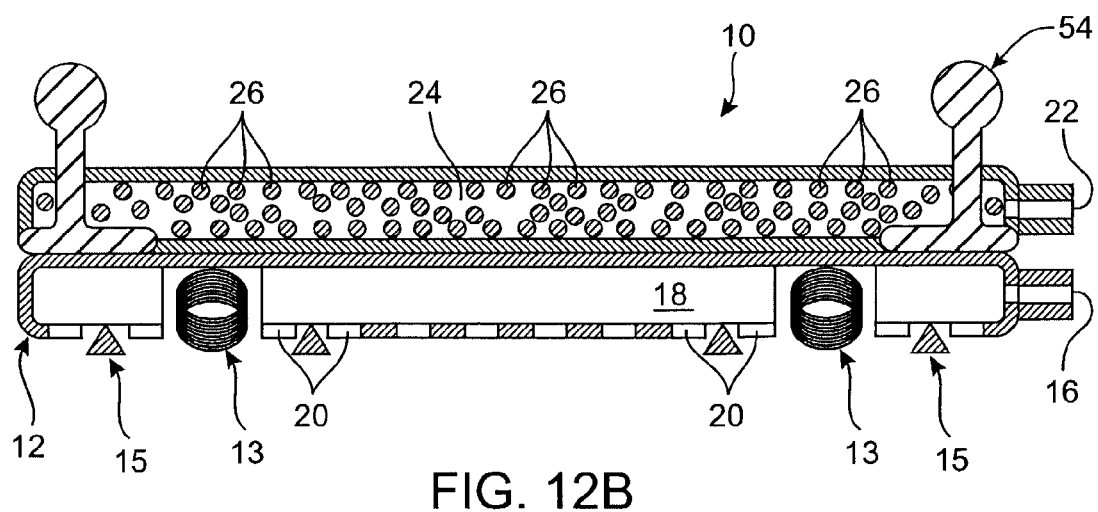
FIG. 12B is a cross-sectional side view of the device in FIG. 12B.

FIGS. 12A and 12B illustrate an embodiment including two engaging structures 54 disposed at corners of device 10. Such engaging structures 54 may be coupled with two separate rigid plates 52, rather than one rigid plate 52. Multiple rigid plates 52 may allow device 10 to be manipulated more freely and perhaps even rolled up cylindrically and introduced to a treatment site via a trocar sheath (FIG. 11).

Figure 13A:
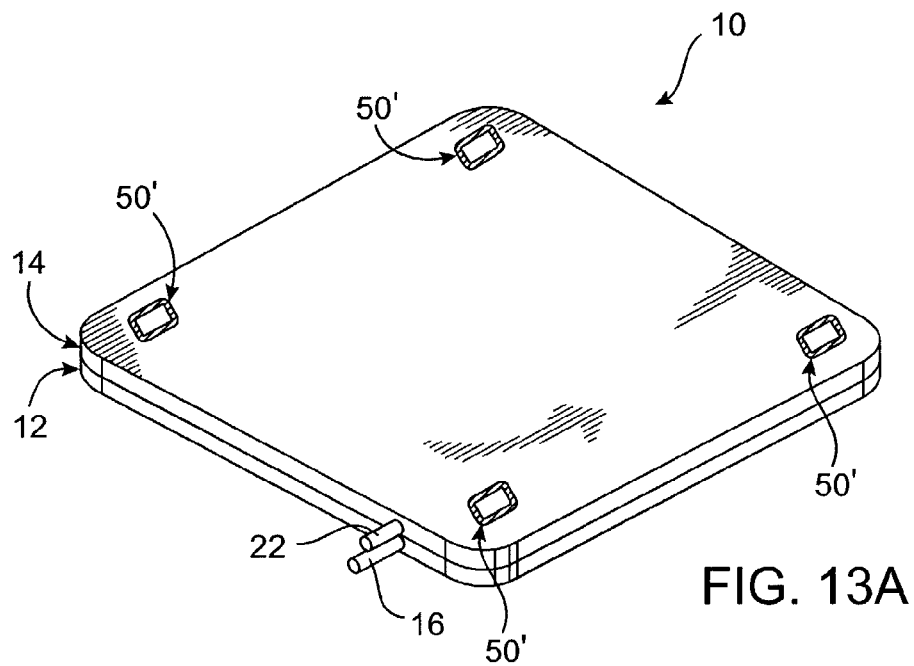
FIGS. 13A-B are perspective views of still another embodiment of a cardiac stabilization and ablation device of the present invention which may be inserted into a body through a trocar sheath.
Figure 13B:
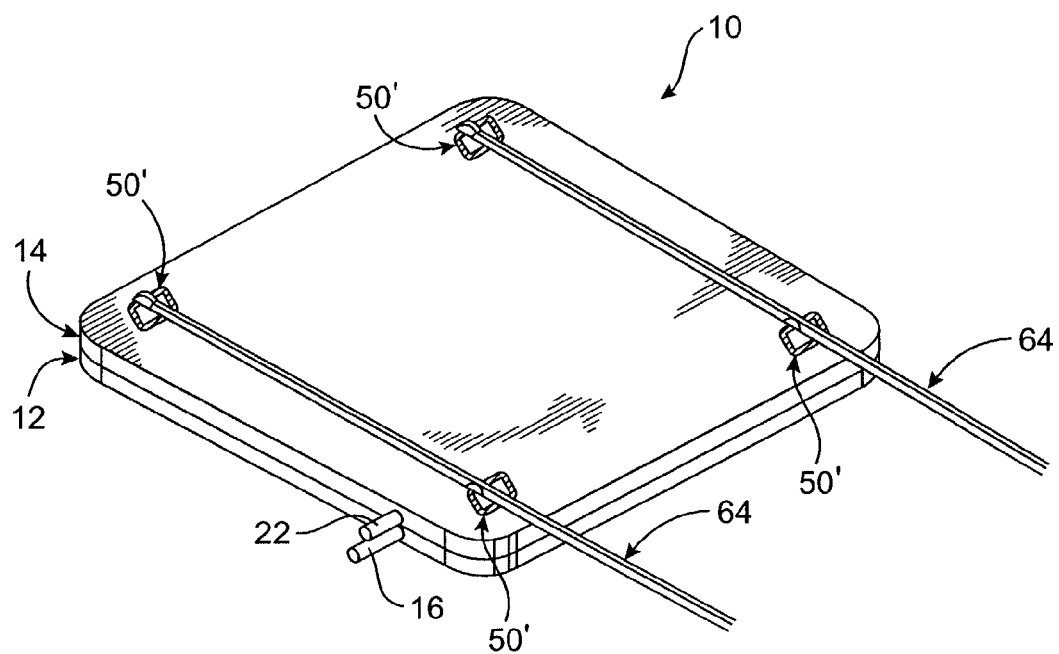

In FIGS. 13A and 13B, device 10 is shown with multiple external retaining structures 50'. External retaining structures 50' may be used when a flexible device 10 is desired, for example when device 10 is introduced in a folded or cylindrical form via a trocar sheath. Such an embodiment would typically not include a rigid plate and would be fully flexible. Once positioned on or near a site for treatment of a tissue, device 10 may be coupled, via external retaining structures 50', to one or more positioning devices 64, such as positioning arms. Positioning devices 64 could then be used to place device 10 in a desired position for ablation and could be decoupled from device 10 after use.

Figure 10:
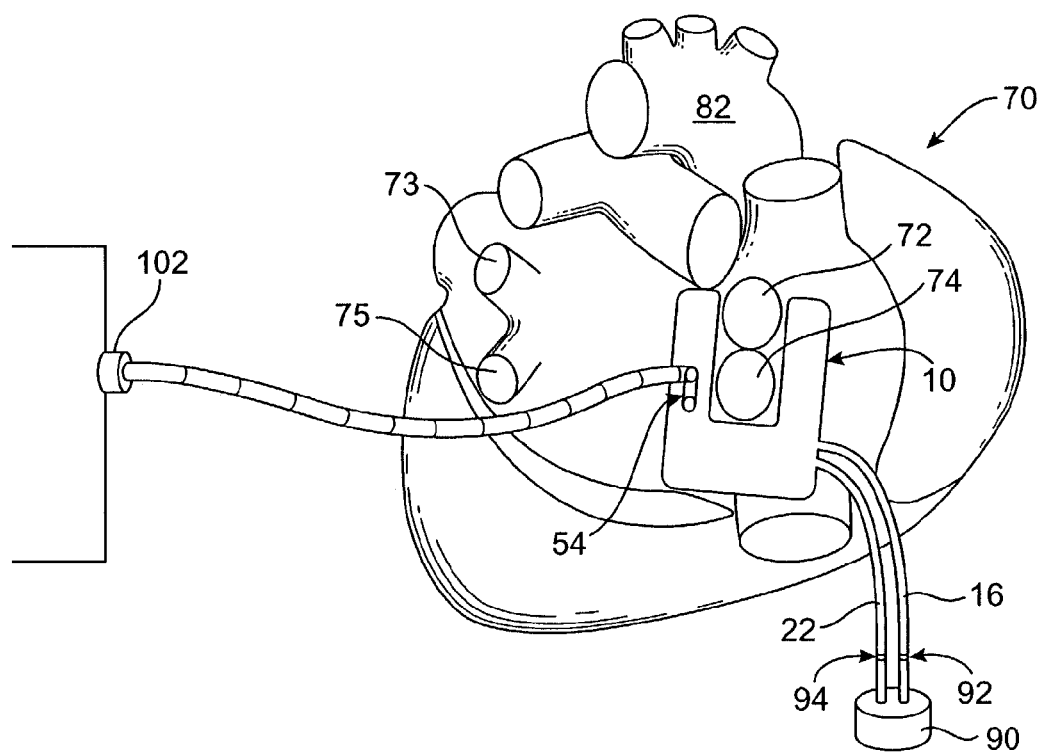
FIG. 10 is a schematic view of a cardiac stabilization and ablation device according to one embodiment of the present invention in use during a cardiac ablation procedure on a heart.

FIG. 10 illustrates an exemplary device 10 as it might be used on a heart 70 to perform a surgical ablation procedure. Anatomical features of heart 70 shown in FIG. 10 include right superior pulmonary vein 72, right inferior pulmonary vein 74, left superior pulmonary vein 73, left inferior pulmonary vein 75 and aorta 82. Device 10 is shown in a position to stabilize and ablate cardiac tissue adjacent right superior pulmonary vein 72 and right inferior pulmonary vein 74. As already discussed, many other configurations and ablation patterns are contemplated within the scope of the present invention.

To perform an ablation procedure on the heart, for example to treat atrial fibrillation, it is advantageous to have a stabilized heart 70. This may be accomplished by placing the patient on a heart-lung machine and stopping the heart from beating with cardioplegia. Alternatively, however, and through use of stabilization/ablation device 10, ablation may be performed on a beating heart without the use of a heart-lung machine.

To advance stabilization/ablation device 10 to an area for positioning and using device 10, access to the heart 70 is first achieved, such as through a medial sternotomy or thoracotomy, which may also involve a retractor. In some embodiments, and with reference now to FIG. 11, access may also be provided in a minimally invasive manner, such as intercostally through a trocar sheath 67 or a "mini" thoracotomy.

With reference again to FIG. 10, device 10 is typically applied to the heart 70 to stabilize the heart 70, thereby providing a stable operating platform for ablation of cardiac tissue. Ports 16 and 22 are connected to a source for suction, such as wall suction 90. Device 10 may include a pair of valves 92 and 94 for regulating the suction between the wall suction 90 and ports 16 and 22, respectively. Device 10 may then be positioned on the epicardium of the heart 70 in a position to provide a desired ablation pattern. When in a desired position for ablation, suction may be applied at port 16 of the attaching bladder 12 by, for example, actuating valve 92, thereby attaching or securing device 10 to the epicardium of heart 70.

The suction applied to port 16 is at a level which minimizes or substantially prevents trauma to the epicardium. Depending upon the configuration of attaching bladder 12, such as the size and/or number of openings 20, the level of applied suction may range from, for example, about 50 millimeters of mercury (mm Hg) to about 150 mm Hg. This pressure range may be at the lower end of the scale if a relatively large number of openings 20 is provided and at the higher end of the scale if a relatively small number of openings 20 is provided.

The applied suction may attach stabilization/ablation device 10 to heart 70 with a level of force which allows device 10 to be moved or slid across the tissue under hand pressure. This feature facilitates the positioning of device 10 to a desired location. It also enables flexible device 10 to be contoured to the anatomical topography of heart 70, providing optimal contact or incidence of the openings 20 on the surface of the epicardium. Thus, device 10 may conform to a surface of heart, such as epicardium overlying the left atrium, inferior vena cava and right atrium, as shown approximately in FIG. 10, much like a patch, substantially "wrapping" around a portion thereof. The U-shape configuration of device 10 allows a surgeon to place a hand on the device with his or her fingers straddling window 56, which ergonomically facilitates the positioning and contouring thereof. Only one hand is typically needed to position device 10 on heart 70.

Once contoured and positioned as desired, suction may be applied at port 22 of rigidifying bladder 14 by, for example, actuating valve 94, thereby stiffening ablation device 10 and maintaining the desired contour. The suction applied at port 22 is at a level which retards bending and flexing of ablation device 10 under hand pressure. Depending on the configuration of rigidifying bladder 14, such as the size and/or number of free-floating rigidifying structures 26, the level of suction applied at port 22 may range from, for example, about 80 mm Hg to about 120 mm Hg. For many cardiac applications, the suction applied to port 22 is such that stabilizer 10 is rigid to about 5 pounds to 10 pounds of force.

Once suction is applied to both ports 16 and 22 as described above, ablation device 10 is attached and rigid, with heart 70 being in its normal cardiac anatomical position. The tissue of the heart 70 to which ablation device 10 is attached is stabilized. Ablation device 10 may then be moved, thereby also moving heart 70 to a desired position to perform an ablative procedure.

External support structure 96 may include an articulated arm 98 with a socket 100, preferably a quick-release socket as shown, which is releasably engageable with ball 58 of ablation device 10. Although a ball-and-socket arrangement is used for the purposes of this description, any complementary releasable fastening means may be implemented. External support structure 96 may include a sternal retractor or a bed post 104 to which support arm 98 is attachable. Articulated support arm 98 may bendable under sufficient hand force. Alternatively, arm 98 may be substantially flexible for positioning and then made rigid through the use of a tensioning cable mechanism. Although only one support arm 98 is shown, external support structure 96 may include a second support arm attached to a second ball-and-post arrangement of ablation device 10. Once ablation device 10 is retained by the external support structure 96, heart 70 is in a stable position and the ablative procedure may be performed.

In various applications, the level of suction applied to port 16 to attach device 10 to heart 70 may vary. For example, about 100 mm Hg to about 200 mm Hg may be applied to port 16 if a more secure attachment of device 10 to heart 70 is desired and about 50 mm Hg to about 150 mm Hg may be applied to port 16 if less secure attachment is desired.

During an ablation procedure, heart 70 may be repositioned as desired by bending or repositioning articulated arm 98. Alternatively, heart 70 may be repositioned by releasing ablation device 10 from support arm 98, repositioning the device and heart as desired, and then reattaching the device to the arm. After the procedure, device 10 may be detached from the external support structure 96, allowing heart 70 to be returned to the normal cardiac anatomical position. The suction may then be disconnected from ports 16 and 22 by actuating valves 92 and 94. Accordingly, device 10 becomes flexible and unattached to the heart 70 and may be removed. As some patients require more than one ablation, the surgeon may then reapply device 10 to another portion of the heart 70 to perform another procedure.

In a commercial medical embodiment of tissue ablation device 10, bladders 12 and 14 may be made from substantially pneumatically impervious and biocompatible material such as silicone or rubber. Alternatively, inner walls of bladders 12 and/or 14 may be made from one or more porous materials, such as a mesh, to allow collapsing of one or more walls, such as for rigidifying of rigidifying bladder 14. Rigidifying structure 26 may be made from silicone or epoxy material or from metal and may include free-floating metal or epoxy beads. Rigidifying structure 26 may also be made from nylon-reinforced silicone mounted to bladder 14. Retaining structure 54 may be made for stainless steel or other suitably rigid material such as nylon.

The overall dimensions of ablation device 10 configured for cardiac use may be about 10 centimeters (cm) to about 15 cm in width and length and may be about 0.5 cm to about 2 cm in thickness. Window 56 may be about 0.5 cm to about 2 cm in width and at least about 3 cm in length. Openings 20 may be about 0.25 cm to about 1 cm in diameter. Ball 58 may have a diameter of about 0.5 cm to 1 cm and may project above a top surface of stabilizer 10 by about 0.75 cm to about 3 cm.

With reference now to FIG. 11, and as mentioned above, many embodiments of stabilization/ablation device 10 may be sufficiently flexible to allow introduction of device 10 into a patient or into another location for treatment through a trocar sheath 67. Trocar sheath 67 may comprise any laproscopic sheath, introducer sheath, or other similar minimally invasive device for introducing device 10 into a patient and/or to a surgical site in a minimally invasive manner. Device 10 may be introduced by rolling, folding or otherwise adjusting the shape of device 10 to fit within and through trocar sheath 67. Once delivered to a site for treatment, device 10 may then be released from sheath 67 for positioning and treatment.

While the invention has been shown and described with reference to specific embodiments thereof, those skilled in the art will understand that alterations, modifications, additions and the like may be made to the embodiments described above or to other embodiments without departing from the spirit and scope of the invention as defined by the following claims. Accordingly, the present invention is not limited to the embodiments shown and described above.

What is claimed is:

1. A method of stabilizing and ablating body tissue, the method comprising:
   contacting a tissue stabilizer having a non-rigid bladder with the tissue;
   securing the tissue stabilizer to the tissue;
   rigidifying the bladder; and
   applying ablation energy to at least a portion of the tissue through the rigidfied bladder.
2. A method as in claim 1, wherein rigidifying the bladder comprises applying a vacuum to the bladder, wherein the vacuum collapses the bladder to cause the bladder to rigidify.
3. A method as in claim 2, wherein the vacuum is applied to the tissue through at least one aperture in the bladder to enhance securing of the tissue stabilizer to the tissue.
4. A method as in claim 3, wherein the vacuum is applied to the tissue through a separate tissue securing bladder coupled with the rigidified bladder.
5. A method as in claim 3, wherein the vacuum is applied to the tissue through a tissue securing compartment in the rigidified bladder.
6. A method as in claim 1, further comprising:
   engaging at least one engaging member on the tissue stabilizer with at least one positioning device; and
   using the positioning device to position the tissue stabilizer in a location for contacting the tissue.
7. A method as in claim 6, wherein the at least one engaging member comprises at least one post-like member coupled with at least one rigid plate coupled with the bladder.
8. A method as in claim 6, further comprising advancing the tissue stabilizer to a surgical site before the engaging step.
9. A method as in claim 1, wherein the bladder further comprises:
   at least one port;
   a chamber within the bladder in communication with the port; and
   rigidifying structure disposed within the chamber, wherein the rigidifying structure is substantially flexible when no suction is applied at the port and substantially rigid when suction is applied at the port.
10. A method as in claim 9, wherein rigidifying the bladder comprises applying a vacuum at the at least one port.
11. A method as in claim 1, wherein applying ablation energy comprises ablating epicardial tissue adjacent at least one pulmonary vein.
12. A method as in claim 11, wherein the epicardial tissue comprises tissue at least partially encircling two pulmonary veins.
13. A method as in claim 1, wherein applying ablation energy comprises transmitting energy to the portion of the tissue, the transmitted energy selected from the group consisting of radio frequency energy, ultrasound energy, microwave energy and cryogenic energy.
14. A method as in claim 13, wherein transmitting energy comprises transmitting radio frequency energy from at least one radio frequency coil.
15. A method as in claim 14, wherein the radio frequency coil is approximately U-shaped so as to contact epicardial tissue adjacent at least two pulmonary veins.
16. A method as in claim 14, further comprising contacting a retractable portion of the radio frequency coil with heart tissue encircling at least two pulmonary veins.
17. A method as in claim 14, wherein the radio frequency coil comprises multiple linear radio frequency coils for ablating a linear pattern on the epicardial tissue.
18. A method as in claim 13, wherein transmitting energy comprises transmitting cryogenic energy from multiple thermoelectric chips.
19. A method as in claim 1, further comprising sensing, with the at least one sensor, an amount of ablation of the tissue.
20. A method as in claim 19, wherein sensing comprises:
   transmitting a radio frequency signal across an area of ablated tissue with a paired sensor; and
   receiving the radio frequency signal at a second paired sensor.

21. A method as in claim 1, further comprising cooling the tissue stabilizer using a cooling member.

22. A method as in claim 21, wherein cooling the stabilizer comprises passing a cooling fluid through the cooling member.

23. A method as in claim 1, further comprising delivering the tissue stabilizer through a minimally invasive introducer device to a location for contacting the tissue.

* * * * *